United States Patent
Sell

(10) Patent No.: US 8,419,681 B2
(45) Date of Patent: Apr. 16, 2013

(54) MAGNETICALLY NAVIGABLE BALLOON CATHETERS

(75) Inventor: Jonathan C. Sell, Eagan, MN (US)

(73) Assignee: Stereotaxis, Inc., St. Louis, MO (US)

( * ) Notice: Subject to any disclaimer, the term of this patent is extended or adjusted under 35 U.S.C. 154(b) by 2935 days.

(21) Appl. No.: 11/131,476

(22) Filed: May 17, 2005

(65) Prior Publication Data

US 2005/0273130 A1 Dec. 8, 2005

Related U.S. Application Data

(63) Continuation of application No. PCT/US03/37222, filed on Nov. 18, 2003.

(60) Provisional application No. 60/427,304, filed on Nov. 18, 2002.

(51) Int. Cl.
*A61M 31/00* (2006.01)
*A61M 37/00* (2006.01)
*A61M 25/098* (2006.01)
*A61F 2/06* (2006.01)

(52) U.S. Cl.
USPC ........................ 604/103.1; 604/529; 623/1.11

(58) Field of Classification Search ............... 604/96.01, 604/102.01–102.03, 103.05, 103.1, 104, 604/529; 606/191–195, 198, 106; 623/1.11; 600/12, 421, 422, 426, 407, 425, 427
See application file for complete search history.

(56) References Cited

U.S. PATENT DOCUMENTS

| | | | |
|---|---|---|---|
| 3,043,309 A * | 7/1962 | McCarthy | 604/540 |
| 4,946,466 A * | 8/1990 | Pinchuk et al. | 606/194 |
| 4,998,917 A * | 3/1991 | Gaiser et al. | 604/103.13 |
| 5,197,978 A * | 3/1993 | Hess | 623/1.18 |
| 5,484,409 A * | 1/1996 | Atkinson et al. | 604/103.03 |
| 5,623,943 A * | 4/1997 | Hackett et al. | 600/585 |
| 5,654,864 A | 8/1997 | Ritter et al. | |
| 5,706,827 A * | 1/1998 | Ehr et al. | 600/585 |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |

(Continued)

*Primary Examiner* — Nicholas Lucchesi
*Assistant Examiner* — Jenna Zhang
(74) *Attorney, Agent, or Firm* — Harness, Dickey & Pierce, P.L.C.

(57) ABSTRACT

A balloon catheter comprising an elongate tube having a proximal end and a distal end, and a lumen therebetween, and a balloon at the distal end of the tube, in fluid communication with the lumen. A magnetically responsive element at the distal end of the device sized and shaped to orient the distal end of the device in an operating region in a subject upon the application of a magnetic field from an external source magnet.

28 Claims, 7 Drawing Sheets

U.S. PATENT DOCUMENTS

| | | |
|---|---|---|
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 2001/0038683 A1 | 11/2001 | Ritter et al. |
| 2002/0019644 A1 | 2/2002 | Hastings et al. |
| 2002/0177789 A1 | 11/2002 | Ferry et al. |
| 2004/0006301 A1 | 1/2004 | Sell et al. |
| 2004/0019447 A1 | 1/2004 | Shachar |
| 2004/0064153 A1 | 4/2004 | Creighton, IV et al. |
| 2004/0068173 A1 | 4/2004 | Viswanathan |
| 2004/0096511 A1 | 5/2004 | Harburn et al. |
| 2004/0133130 A1 | 7/2004 | Ferry et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2005/0020911 A1 | 1/2005 | Viswanathan et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2006/0009735 A1 | 1/2006 | Viswanathan et al. |
| 2006/0025679 A1 | 2/2006 | Viswanathan et al. |
| 2006/0036125 A1 | 2/2006 | Viswanathan et al. |
| 2006/0036163 A1 | 2/2006 | Viswanathan |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0093193 A1 | 5/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |

\* cited by examiner

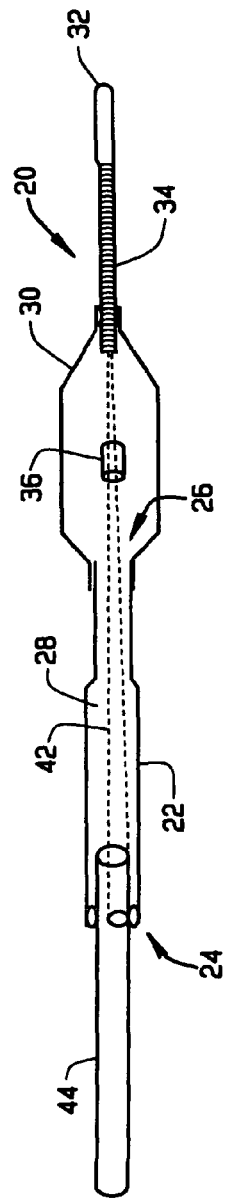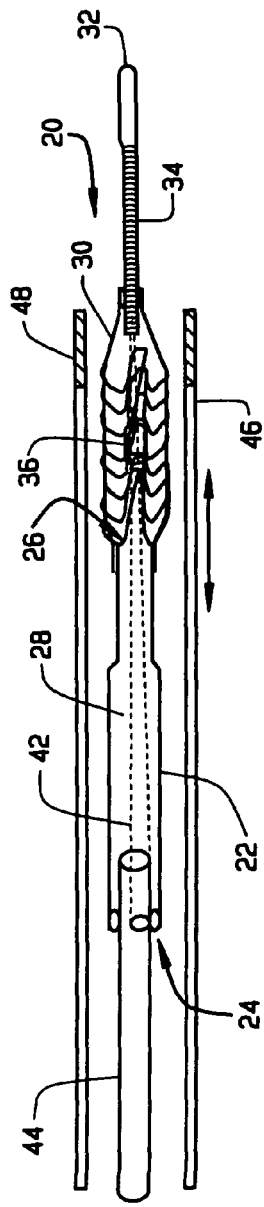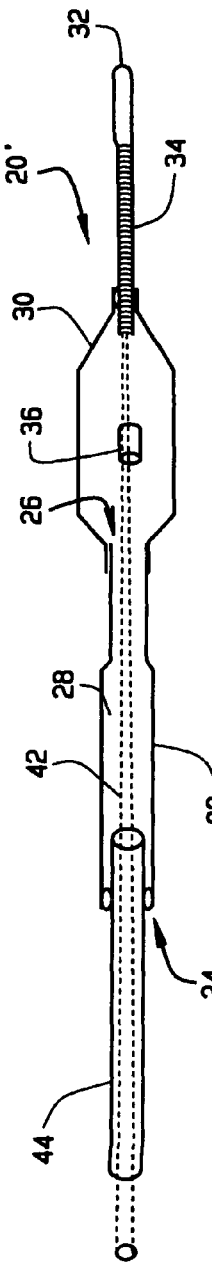

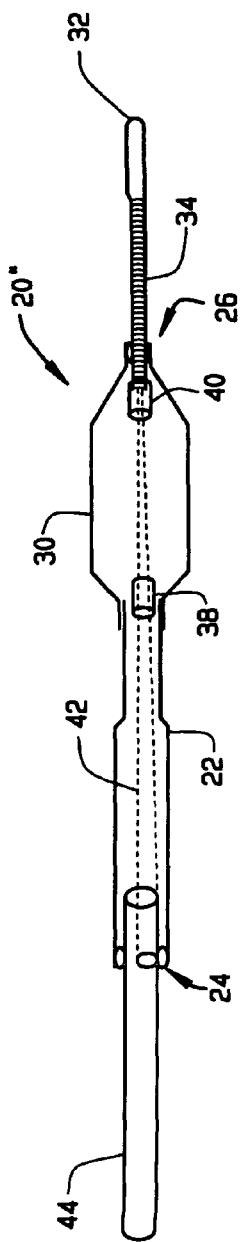
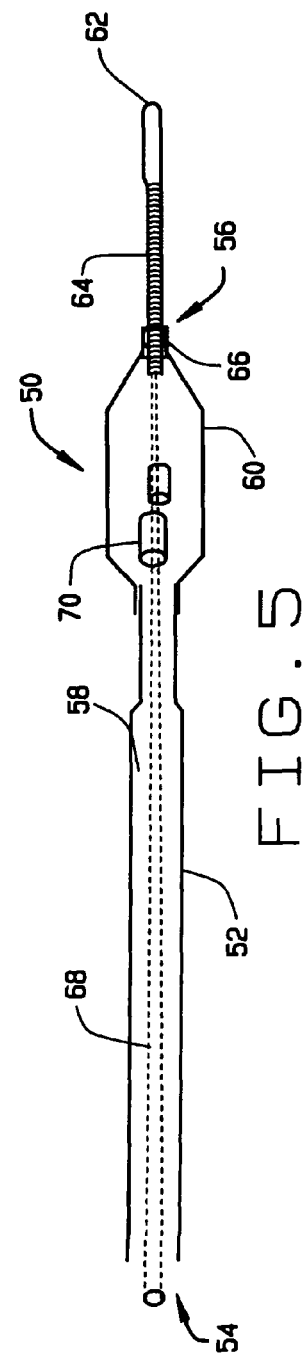
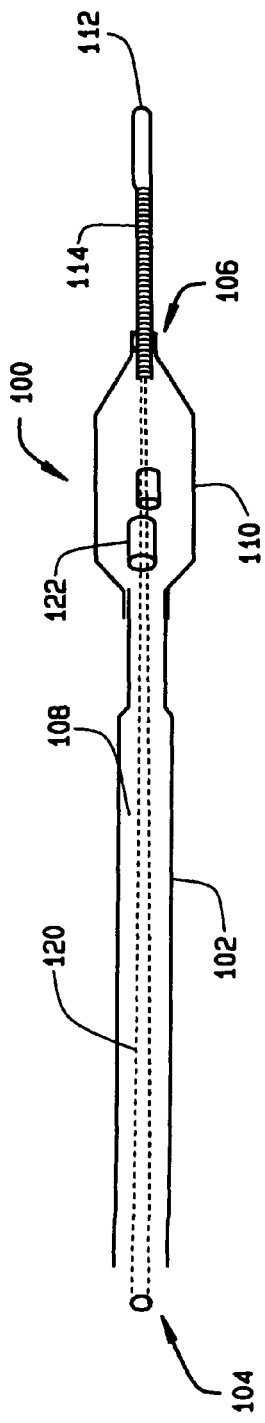

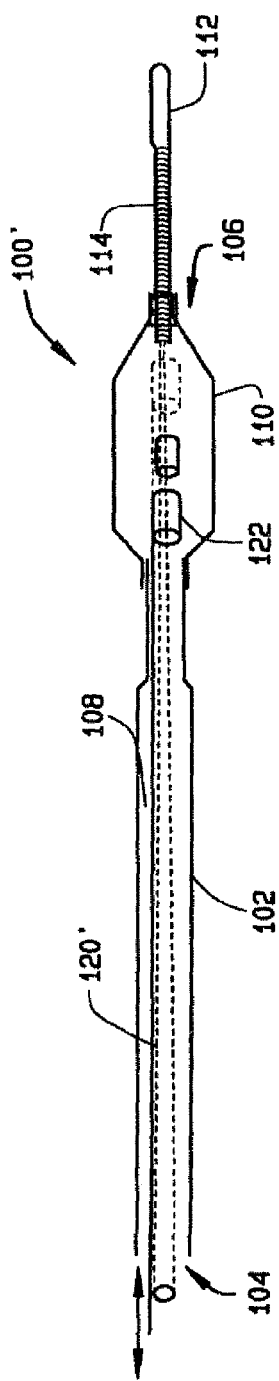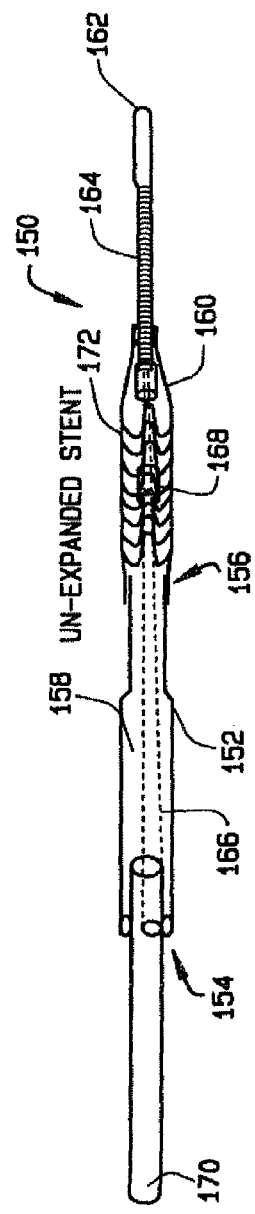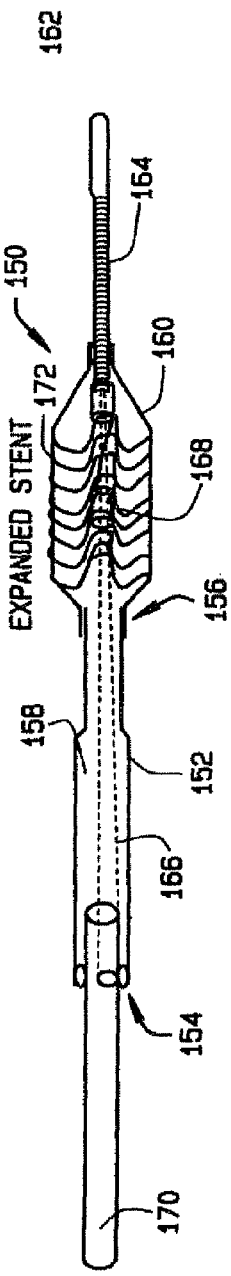

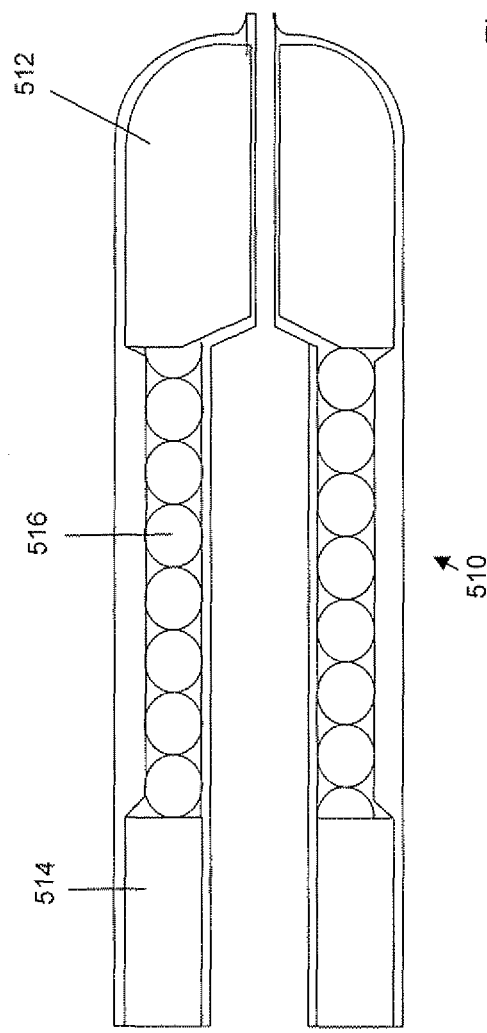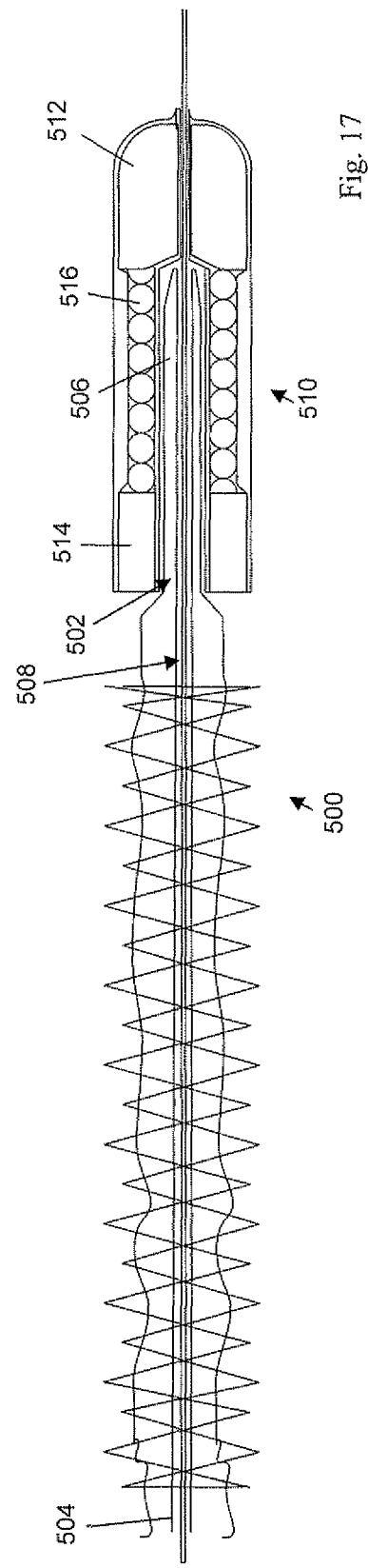

MAGNETICALLY NAVIGABLE BALLOON CATHETERS

BACKGROUND OF THE INVENTION

This invention relates to balloon catheters, such as those used in angioplasty and stent delivery, and in particular to magnetically navigable balloon catheters.

Balloon catheters, i.e. catheters have an expandable balloon adjacent their distal ends have found a number of medical applications. For example in angioplasty, the catheter is navigated into a partially closed blood vessel and the balloon is inflated both to stretch the vessel and to compress the atheromatous material on the vessel wall, thereby widening the vessel to increase blood flow. Balloon catheters are also used in a similar procedure in which a stent is placed in the blood vessel to help keep the vessel open. The catheter with a compressed stent over the balloon is navigated to the desire site of placement, and the balloon is inflated to expand the stent in the vessel. These and other procedures employing balloon catheters are value and important procedures that can extend lives and improve quality of life, but whose use, however, is limited by the difficult of navigating the catheters in the small and partially blocked vessels. The balloon, and particularly a balloon and stent, can be very difficult to navigate using conventional means. The sharp changes in flexibility of the catheter, particularly at the proximal and distal ends of the balloon make it difficult to direct the catheter into certain. To overcome some of the navigation issues, manufacturers of stents have lowered the amount of metal contained in a stent in order to make them more flexible at the possible expense of optimum vessel scaffolding and coverage. A tool that can improve the navigability of less flexible stents is desirable.

One of the embodiments of the invention is a self expanding stent. This is a stent that automatically expands when delivered to the site of the occlusion. These are typically constrained by a sheath that is retracted once the stent has been delivered to the correct location. Retraction of the sheath then allows the stent to reach its normally open configuration and keep the vessel open.

SUMMARY OF THE INVENTION

The present invention relates to magnetically navigable balloon catheter that can be more easily navigated using an external source magnet to align the distal end of the balloon catheter in a selected direction so that the catheter can be advanced to the desired location. Generally, magnetically navigable balloon catheter of the present invention comprises an elongate tube having a proximal end and a distal end, and a lumen therebetween. A balloon is disposed at the distal end of the tube, in fluid communication with the lumen. The balloon can be formed integrally from the tube, or made of a separate piece attached to tube. A magnetically responsive element is disposed at the distal end of the device, the element is sized and shaped to orient the distal end of the device in an operating region in a subject upon the application of a magnetic field from an external source magnet.

In accordance with one preferred embodiment, there is a coil of magnetically responsive material between the balloon and the magnetically responsive element. The proximal end of this coil preferably extends into the distal end of the balloon. This coil can include or be coated with a radiopaque material. Instead of a magnetically responsive material, the coil could simply be made of a radiopaque material.

The balloon catheter can also include one or more radiopaque marker bands for identifying the position of the balloon under fluoroscopic visualization. A radiopaque marker band can be provided intermediate the proximal and distal ends of the balloon, alternatively, or in addition a radiopaqe marker band at at least one of the proximal and distal ends of the balloon.

A core wire can be provided in the catheter to control the stiffness of the catheter. The core wire preferably tapers from at least a point proximal to the balloon, to the distal end of the balloon.

An expandable stent can be provided on the on the exterior of the balloon.

The balloon catheter also may include one or more magnetically responsive elements inside the balloon. These magnetically responsive elements can be provided on a core wire extending through the balloon. The core wire can be made movable so that the magnets can be moved.

In still another embodiment, a guide wire channel, having a proximal end and a distal end, and extending at least partly through the lumen of the elongate tube to the distal end of the balloon catheter is provided for use with a guide wire. A tubular magnetically responsive element is provided at the distal end of the guide wire channel. This magnetically responsive element can be disposed at least partly within the balloon.

An additional embodiment is a self-expanding stent delivery catheter an outer elongate tube having a proximal end and a distal end, and a lumen therebetween. A core element consisting of a tube or solid core wire runs inside of the outer elongate tube along at least part of its length. The distal end of the core element has decreasing flexibility near its distal end. A means is provided to allow longitudinal movement of the outer elongate tube relative to the core element. A self expanding stent located between the outer elongate tube and core element. A magnetically responsive element is disposed at the distal end of the device, the element is sized and shaped to orient the distal end of the device in an operating region in a subject upon the application of a magnetic field from an external source magnet.

The magnetically responsive and radiopaque elements allow the distal end of the balloon catheter to be oriented with an externally applied magnetic field. The balloon catheter can be constructed to reduce sharp discontinuities in flexibility that impair navigation through the vasculature, including for example, a tapering core wires and/or a flexible coil. Thus the use of balloon catheters is made easier for many procedures, and is made available for many more procedures at locations where conventional balloon catheters could not easily be navigated.

BRIEF DESCRIPTION OF THE DRAWINGS

FIG. 1 is a longitudinal cross-sectional view of a first embodiment of a balloon catheter constructed according to the principles of this invention;

FIG. 2 is a longitudinal cross-sectional view of the balloon catheter of the first embodiment, in a magnetically-tipped retractable sheath;

FIG. 3 is a longitudinal cross-sectional view of a first alternate construction of the balloon catheter constructed according to the principles of this invention;

FIG. 4 is a longitudinal cross-sectional view of a second alternate construction of the balloon catheter constructed according to the principles of this invention;

FIG. 5 is a longitudinal cross-sectional view of a second embodiment of a balloon catheter constructed according to the principles of this invention;

FIG. 6 is a longitudinal cross-sectional view of a third embodiment of a balloon catheter constructed according to the principles of this invention;

FIG. 7 is a longitudinal cross-sectional view of a first alternate construction of the balloon catheter of the third embodiment;

FIG. 8 is a longitudinal cross-sectional view of a fourth embodiment of a balloon catheter constructed according to the principles of this invention, with a stent over the balloon;

FIG. 9 is a longitudinal cross-sectional view of the balloon catheter of the fourth embodiment, with the balloon expanded;

FIG. 17 is a longitudinal cross-sectional view of a balloon catheter with an attachable/detachable magnet for adaptation to magnetic navigation, in accordance with an eighth embodiment of this invention; and FIG. 18 is an enlarged longitudinal cross-sectional view of an attachable/detachable magnet as shown in FIG. 17.

Corresponding reference numerals indicate corresponding parts throughout the drawings.

DETAILED DESCRIPTION OF THE INVENTION

Figure 10:
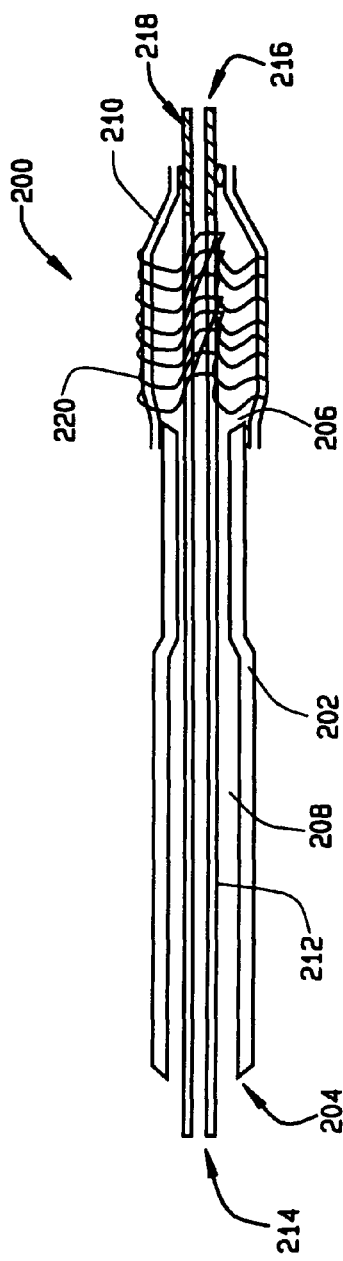
FIG. 10 is a longitudinal cross-sectional view of a fifth embodiment of a balloon catheter constructed according to the principles of this invention.

A first embodiment of a magnetically guidable balloon catheter constructed according to the principles of this invention is indicated generally as 20 in FIG. 1. FIG. 2 shows the balloon catheter 20 in a sheath, as described in more detail below. A first alternate construction of the first embodiment is indicated generally as 20' in FIG. 3, and a second alternate construction of the first embodiment is indicated generally as 20" in FIG. 4.

As shown in FIG. 1, balloon catheter 20 comprises elongate flexible tube 22 having a proximal end 24 and a distal end 26, and a lumen 28 therebetween. There is a balloon 30 at the distal end 26 of the tube 22, in fluid communication with the lumen 28. A magnetically responsive element 32 is provided at the distal end of the balloon catheter. The magnetically responsive element 30 is sized and shaped to orient the distal end of the catheter in an operating region in a subject upon the application of a magnetic field from an external source magnet.

The magnetically responsive element 32 may be made of a permanent magnetic material, such as hiperco, or a permanent magnetic material such as neodymium-iron-boron, or other suitable materials. The element 32 is preferably sized to align with an applied magnetic field of no more than about 0.3 T, more preferably, no more than about 0.2 T, and most preferably less than about 0.1 T.

As shown in FIG. 1, in this first embodiment a flexible, radiopaque element 34 can be provided between the magnetically responsive element 32 and the balloon 30. The radiopaque element 34 is preferably a flexible coil. This coil can be made of a radiopaque material, or it can be a non-radiopaque material coated with a radiopaque material. For example the element 34 could be made of a magnetically permeable material such as hiperco, plated with gold. Making the radiopaque element out of a permeable magnetic material help control and orient the distal end of the balloon 30 in an applied magnetic field. As shown in FIG. 1, the proximal end of the element 34 extends proximally of the distal end of the balloon 30. This overlap helps location of the distal end of the balloon 30 in fluoroscopic images, and if made of a magnetically responsive element, also helps control the distal of the balloon.

As also shown in FIGS. 1-4, the balloon catheter 20 of this first embodiment preferably also includes one or more additional radiopaque marker bands for identifying the position of the balloon on fluoroscopic images. As shown in FIGS. 1-3, a marker band 36 is provided intermediate the proximal and distal ends of the balloon 30. However, a marker band can alternatively or additionally be provided at one or both ends of the balloon. As shown in FIG. 4, a marker band 38 is provided at the proximal end of the balloon, and a marker band 40 is provided at the distal end of the balloon. The marker bands could be additional magnetically responsive elements, coated with a radiopaque material, for example hiperco elements coated with gold.

The balloon catheter can also include a core wire. As shown in FIGS. 1-4, a core wire 42 is disposed inside the balloon catheter. The core wire helps control the stiffness/flexibility of the device, reducing sharp discontinuities in flexibility that could interfere with the navigation of the balloon catheter. In the first preferred embodiment, the core wire 42 tapers in the distal direction from a point proximal to the balloon to the distal end of the balloon 30. The radiopaque marker bands 36 (FIGS. 1-3) and 38 and 40 (FIG. 4) are mounted on the core wire 42.

As shown in FIGS. 1-4, the proximal end of the flexible tube 22 is secured to the distal end of a proximal tube 44, for example with an adhesive, with sonic welding, or any other suitable means. As shown in FIGS. 1, 2, and 4, the core wire 42 extends to the juncture between the proximal tube 44 and the flexible tube 22. Alternatively, as shown in FIG. 3, the core wire 42 can extend to the proximal end of the proximal tube 44.

As shown in FIGS. 1-3, the balloon 30 can be a separate element secured onto the distal end 26 of the flexible tube 22. However, as shown in FIG. 4, the balloon 30 could be formed integrally with the tube 22.

FIG. 2 shows the balloon catheter 20 disposed in a delivery sheath 46, having a tubular magnetic tip 48. The balloon catheter 20 and sheath 46 can be navigated to the procedure site with the magnet 32 and radiopaque element 34 extending from the distal end of the sheath 46.

A second embodiment of a balloon catheter constructed according to the principles of this invention is indicated generally as 50 in FIG. 5. As shown in FIG. 5, the balloon catheter comprises elongate flexible tube 52 having a proximal end 54 and a distal end 56, and a lumen 58 therebetween. There is a balloon 60 at the distal end 56 of the tube 52, in fluid communication with the lumen 58. In this second preferred embodiment, the balloon 60 is made integrally with the tube 52. A magnetically responsive element 62 is provided at the distal end of the balloon catheter 50. As with element 32 of the first embodiment, the magnetically responsive element 62 is sized and shaped to orient the distal end of the catheter in an operating region in a subject upon the application of a magnetic field from an external source magnet.

Like element 32 of the first embodiment, the magnetically responsive element 62 may be made of a permanent magnetic material, such as hiperco, or a permanent magnetic material such as neodymium-iron-boron, or other suitable materials. The element 62 is preferably sized to align with an applied magnetic field of no more than about 0.3 T, more preferably, no more than about 0.2 T, and most preferably less than about 0.1 T.

As shown in FIG. 5, in this second embodiment a flexible, radiopaque element 64 can be provided between the magnetically responsive element 62 and the balloon 60. The radiopaque element 64 is preferably a flexible coil. This coil can be made of a radiopaque material, or it can be a non-radiopaque material coated with a radiopaque material. For example the element 64 could be made of a magnetically permeable material such as hiperco, plated with gold. Making the radiopaque element out of a permeable magnetic material help control and orient the distal end of the balloon 60 in an applied magnetic field. As shown in FIG. 5, a second magnetically responsive element 66 is provided at the proximal end of the element 64, distal to the balloon 60.

The balloon catheter 50 also includes a core wire 68, disposed inside the balloon catheter. The core wire 68 helps control the stiffness/flexibility of the device, reducing sharp discontinuities in flexibility that could interfere with the navigation of the balloon catheter. In the second preferred embodiment, the core wire 68 tapers in the distal direction from a point proximal to the balloon to the distal end of the balloon 60. An additional magnetically responsive element 70 can be provided in the balloon 60, on the core wire 68. The element 70 can be similar to the elements 62 and 66 described above. Each of the magnetically responsive elements 62, 66 and 70 can also be made radiopaque, for example by coating with gold.

A third embodiment of a balloon catheter constructed according to the principles of this invention is indicated generally as 100 in FIG. 6. As shown in FIG. 6, balloon catheter 100 comprises elongate flexible tube 102 having a proximal end 104 and a distal end 106, and a lumen 108 therebetween. There is a balloon 110 at the distal end 106 of the tube 102, in fluid communication with the lumen 108. As shown in FIG. 6, a magnetically responsive element 112 is provided at the distal end of the balloon catheter 100. The magnetically responsive element 112, like element 32 of the first embodiment and element 62 of the second embodiment, is sized and shaped to orient the distal end of the catheter in an operating region in a subject upon the application of a magnetic field from an external source magnet.

The magnetically responsive element 112, like elements 32 of the first embodiment and 62 of the second embodiment, may be made of a permanent magnetic material, such as hiperco, or a permanent magnetic material such as neodymium-iron-boron, or other suitable materials. The element 112 is preferably sized to align with an applied magnetic field of no more than about 0.3 T, more preferably, no more than about 0.2 T, and most preferably less than about 0.1 T.

As shown in FIG. 6, in this third embodiment a flexible element 114 is provided between the magnet element 112 and the balloon 110, made of a magnetically permeable material such as hiperco. The element 114 can be made radiopaque, for example with gold plating. As shown in FIG. 6, the proximal end of the element 114 extends proximally of the distal end of the balloon 110. This overlap helps control the distal of the balloon, and if element 114 is made of a radiopaque material it helps locate the distal end of the balloon 110 in fluoroscopic images.

The balloon catheter 100 can also include a core wire. As shown in FIG. 6, a core wire 120 is disposed inside the balloon catheter. The core wire 120 helps control the stiffness/flexibility of the device, reducing sharp discontinuities in flexibility that could interfere with the navigation of the balloon catheter. In this third preferred embodiment, the core wire 120 tapers in the distal direction from a point proximal to the balloon to the distal end of the balloon 110. An additional magnetically responsive element 122 can be provided in the balloon, on the core wire 120. The element 122 can be similar to the element 112 described above. The magnetically responsive elements can also be made radiopaque, for example by coating with gold.

A first alternate construction of the third embodiment indicated generally as 100' is shown in FIG. 7, in which a magnet contained within the balloon 122 is movable relative to the balloon 110, to change the magnetic responsiveness of distal end portion of the balloon catheter 100'.

A fourth embodiment of a balloon catheter is indicated generally as 150 in FIGS. 8 and 9. As shown in FIGS. 8 and 9, balloon catheter 150 comprises elongate flexible tube 152 having a proximal end 154 and a distal end 156, and a lumen 158 therebetween. There is a balloon 160 at the distal end 156 of the tube 152, in fluid communication with the lumen 158. A magnetically responsive element 162 is provided at the distal end of the balloon catheter. As with element 32 of the first embodiment, element 62 of the second embodiment, and element 112 of the third embodiment, the magnetically responsive element 162 is sized and shaped to orient the distal end of the catheter in an operating region in a subject upon the application of a magnetic field from an external source magnet.

As with element 32 of the first embodiment, element 62 of the second embodiment, and element 112 of the third embodiment, the magnetically responsive element 162 may be made of a permanent magnetic material, such as hiperco, or a permanent magnetic material such as neodymium-iron-boron, or other suitable materials. The element 162 is preferably sized to align with an applied magnetic field of no more than about 0.3 T, more preferably, no more than about 0.2 T, and most preferably less than about 0.1 T.

As shown in FIGS. 8 and 9, in this fourth embodiment a flexible, magnetically responsive coil 164 can be provided between the magnet element 162 and the balloon 160. For example the element 164 could be made of a magnetically permeable material such as hiperco, plated with gold. Making the radiopaque element out of a permeable magnetic material help control and orient the distal end of the balloon 160 in an applied magnetic field. As shown in FIGS. 8 and 9, the proximal end of the element 164 extends proximally of the distal end of the balloon 160. This overlap helps control the distal of the balloon, and if coated with a radiopaque material, helps locate the distal end of the balloon.

One or more additional radiopaque marker bands for identifying the position of the balloon on fluoroscopic images can be provided, if desired.

The balloon catheter 150 can also include a core wire 166. As shown in FIGS. 8 and 9, the core wire 166 is disposed inside the balloon catheter. The core wire 166 helps control the stiffness/flexibility of the device, reducing sharp discontinuities in flexibility that could interfere with the navigation of the balloon catheter. In this fourth preferred embodiment, the core wire 166 tapers in the distal direction from a point proximal to the balloon to the distal end of the balloon 160. An additional magnetically responsive element 168 can be provided in the balloon, on the core wire 164. The element 168 can be similar to the element 110 described above. The magnetically responsive elements can also be made radiopaque, for example by coating with gold As shown in FIGS. 8 and 9, the proximal end 154 of the flexible tube 152 is secured to the distal end of a proximal tube 170, for example with an adhesive, with sonic welding, or any other suitable means. As shown in FIGS. 8 and 9, the core wire 166 extends to the juncture between the proximal tube 170 and the flexible tube 152. Alternatively, as shown in FIGS. 3, 8 and 9, the core wire 166 can extend to the proximal end of the proximal tube 170.

As shown in FIGS. 8 and 9, the balloon 160 can be a separate element secured onto the distal end of the flexible tube 152. However, the balloon 160 could be formed integrally with the tube 152.

As shown in FIG. 8, an expandable stent 172 is secured over the balloon 160. As shown in FIG. 9, expansion of the balloon 160 causes the stent 172 to permanently expand, placing it in the vasculature or other passage or duct in the body.

A fifth embodiment of a balloon catheter constructed according to the principles of this invention is indicated generally as 200 in FIG. 10. As shown in FIG. 10, the balloon catheter 200 comprises elongate flexible tube 202 having a proximal end 204 and a distal end 206, and a lumen 208 therebetween. There is a balloon 210 at the distal end 206 of the tube 204, in fluid communication with the lumen 208. A guide wire channel 212, having a proximal end 214, and a distal end 216, and extending at least partly through the lumen 208 of the elongate tube 202 to the distal end of the balloon catheter 200. A magnetically responsive element 218 is provided at the distal end of the balloon catheter. The element 218 may be a tube of magnetically responsive material at the distal end 216 of the guide wire channel 212. The magnetically responsive element 218 is sized and shaped to orient the distal end of the catheter in an operating region in a subject upon the application of a magnetic field from an external source magnet.

The magnetically responsive element 218 may be made of a permeable magnetic material, such as hiperco, or a permanent magnetic material such as neodymium-iron-boron, or other suitable materials. The element 218 is preferably sized to align with an applied magnetic field of no more than about 0.3 T, more preferably, no more than about 0.2 T, and most preferably less than about 0.1 T.

As shown in FIG. 10, the proximal portion of the magnetically responsive element 218 is disposed in the balloon 210. The element 218 can be made radiopaque, if desired, for example with gold plating, so that the distal end of the balloon catheter 200 can be located in fluoroscopic images. This overlap helps to control the distal end of the balloon, and if radiopaque, helps location of the distal end of the balloon 210 in fluoroscopic images. One or more additional radiopaque marker bands for identifying the position of the balloon on fluoroscopic images.

As shown in FIG. 10, an expandable stent 220 is secured over the balloon 210. As shown in FIG. 10, expansion of the balloon 210 causes the stent to permanently expand, placing it in the vasculature or other passage or duct in the body.

Figure 11:
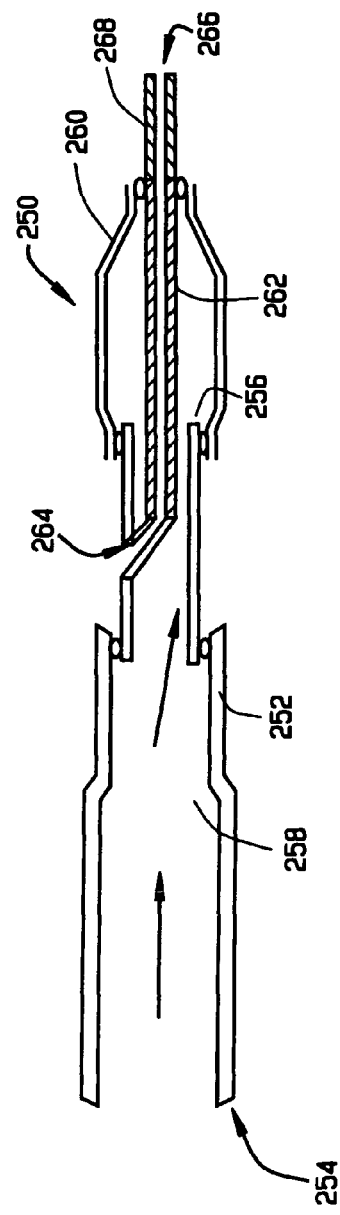
FIG. 11 is a longitudinal cross-sectional view of a sixth embodiment of a balloon catheter constructed according to the principles of this invention.

A sixth embodiment of a balloon catheter constructed according to the principles of this invention is indicated generally as 250 in FIG. 11. As shown in FIG. 11, the balloon catheter 250 comprises elongate flexible tube 252 having a proximal end 254 and a distal end 256, and a lumen 258 therebetween. There is a balloon 260 at the distal end 256 of the tube 252, in fluid communication with the lumen 258. A guide wire channel 262, having a proximal end 264, and a distal end 266, extends at least partly through the lumen 258 of the elongate tube 252 to the distal end of the balloon catheter 250. A magnetically responsive element 268 is provided at the distal end of the balloon catheter. In this sixth preferred embodiment, the element 268 is a tubular element on the distal end of the guide wire channel 262. The magnetically responsive element 268 is sized and shaped to orient the distal end of the catheter in an operating region in a subject upon the application of a magnetic field from an external source magnet.

The magnetically responsive element 268 may be made of a permeable magnetic material, such as hiperco, or a permanent magnetic material such as neodymium-iron-boron, or other suitable materials. The element 268 is preferably sized to align with an applied magnetic field of no more than about 0.3 T, more preferably, no more than about 0.2 T, and most preferably less than about 0.1 T.

As shown in FIG. 11, the proximal end 264 of the guide wire channel 262 opens to the wall of the elongate tube 252 proximal to the balloon 260, for the passage of a guide wire.

Figure 12:
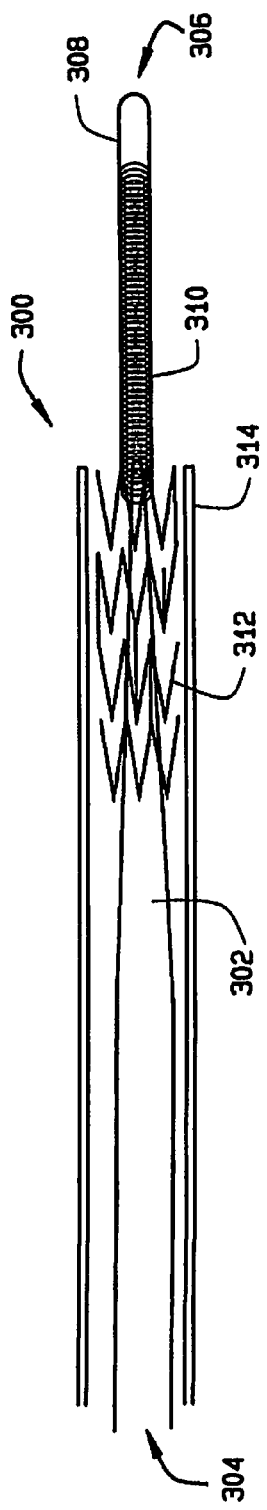
FIG. 12 is longitudinal cross-sectional view of a self-expanding stent on a magnetically navigable guide wire and a delivery sheath, in accordance with a seventh embodiment of the present invention.
Figure 13:
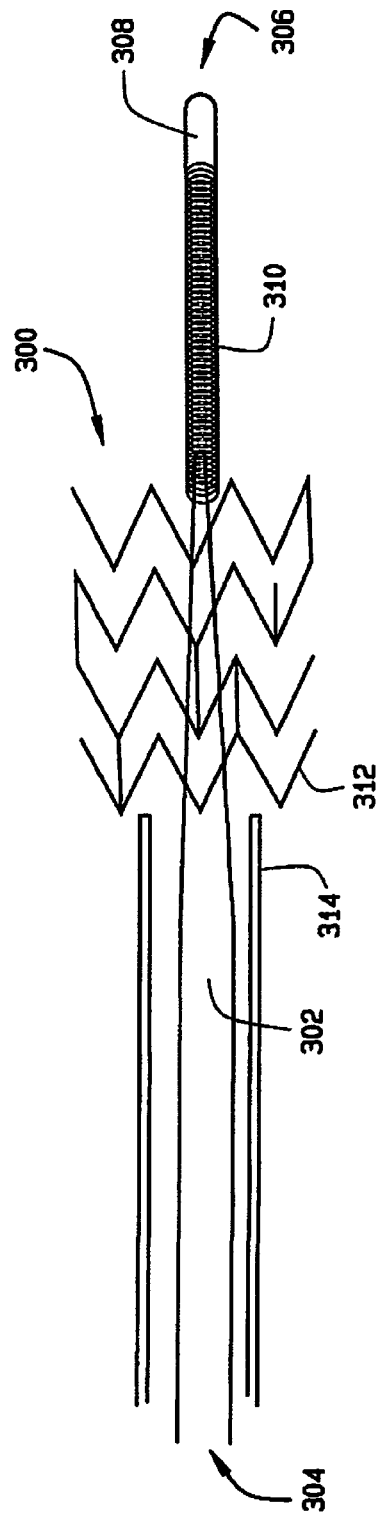
FIG. 13 is a longitudinal cross-sectional view of a self-expanding stent in FIG. 12 after the delivery sheath is retracted.

As shown in FIGS. 12 and 13, stent placement device 300 comprises a tapering guide wire 302, having a proximal end 304, and a distal end 306. A magnetically responsive element 308 is disposed on the distal end 306 of the guide wire, and connected thereto with a flexible coil 310, which is preferably both magnetically responsive, and radiopaque. For example, the coil 310 can be made from hiperco and coated with gold. A self expanding stent 312 is disposed over the distal end portion of the guide wire 302, inside a sheath 314, with the magnetically responsive element 308 and the coil 310 projecting from the distal end of the sheath. The distal end of the sheath is navigated to the stent placement site, with an externally applied magnetic field. Once at the site the sheath 214 is retracted, allowing the stent 312 to expand. The sheath 314 and the guide wire 302 can then be withdrawn.

Figure 14:
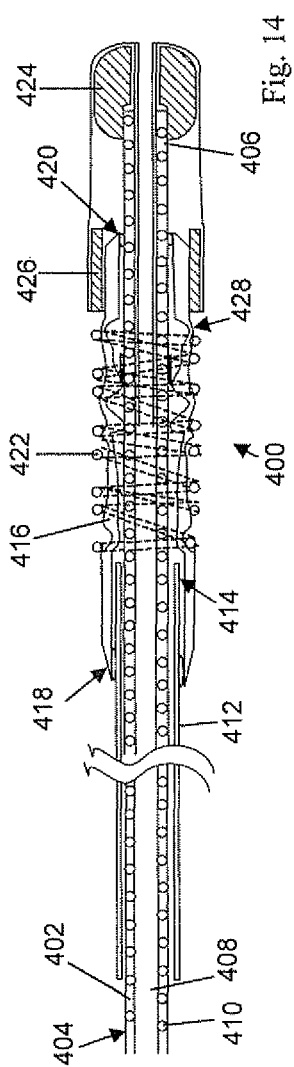
FIG. 14 is a longitudinal cross-sectional view of a balloon catheter constructed according to an eighth embodiment of this invention.
Figure 15:
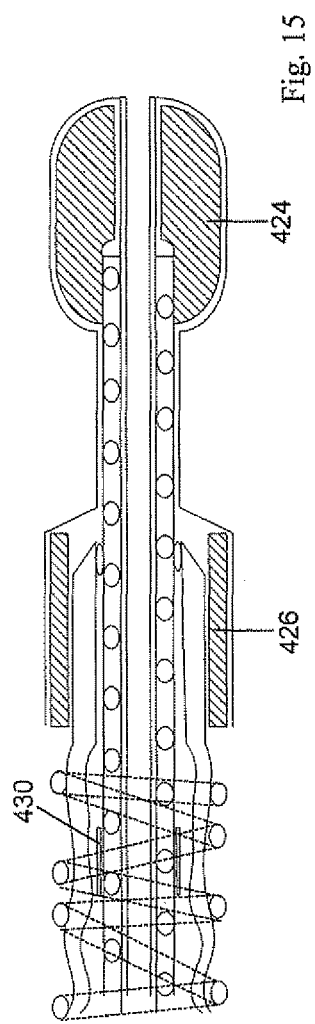
FIG. 15 is an enlarged partial longitudinal cross-sectional view of the balloon catheter of the eighth embodiment.
Figure 16:
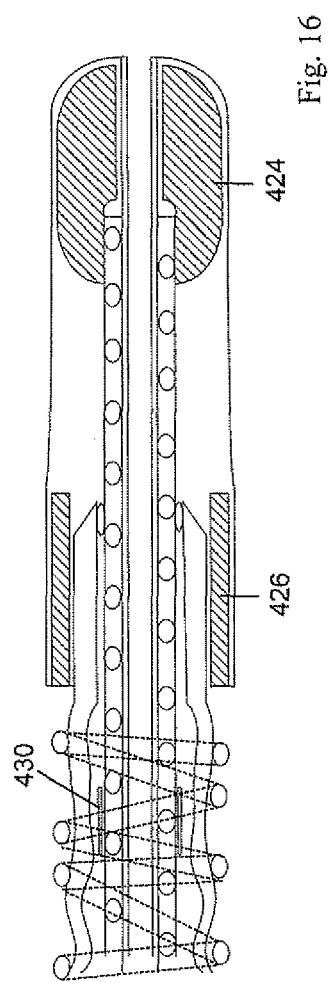
FIG. 16 is an enlarged partial longitudinal cross-sectional view of the balloon catheter of the eighth embodiment.

A seventh embodiment of a balloon catheter is indicated as 400 in FIGS. 14-16. Balloon catheter 400 comprises an elongate flexible tube 402, having a proximal end 404 and a distal end 406 and a lumen 408 therethrough. A flexible coil 410 is preferably embedded in the wall of at least the distal portion of the tube 402. The coil 410 can be made of a magnetically responsive material, either a permeable magnetic material such as hiperco, or a permanent magnetic material such as neodymium-iron-born, to increase the magnetic responsiveness of the balloon catheter 400. A sheath 412 extends over the proximal portion of the tube 402, and the distal end 414 of the sheath 412 ends proximal to the distal end of the tube 402. A balloon 416 has a proximal end 418 sealingly secured to the distal end of the sheath 410, and a distal end 420 sealingly secured to the tube 402 adjacent the distal end 406. An expandable stent 422 is disposed over the balloon 416, such that when the balloon 416 is inflated via the sheath 412, the stent 422 is expanded.

At least one, and this seventh preferred embodiment two, magnetically responsive elements are provided on the distal end of the balloon catheter 400. A first magnetically responsive element 424 is disposed over the distal end of the tube 402, and has a recess in its proximal face for receiving and attaching the tube to the magnet, and a passage therethrough aligned with the lumen of the tube 402. A second magnetically responsive element 426 is disclosed over the catheter, proximal to first element 424. The second element 426 has an annular shape, and is disposed over the distal end 418 of the balloon 416. A lubricated polymer jacket 428 can surround the balloon catheter 400, adjacent its distal end.

The tube 402 and the magnet 424 provide a continuation passage for receiving a guide wire. The magnets 424 and 426 help align the distal end of the catheter 400 in response to an applied magnetic field, and the coil 410 helps prevent kinking of the catheter in the vicinity of the balloon 416, and can contribute to the magnetic responsiveness of the catheter 400.

One or more radiopaque makers 430 can be provided on the distal end of the devices so that the device can be visualized in x-ray and fluoroscope images.

An eighth embodiment of a balloon catheter is indicated generally as 500 in FIGS. 17 and 18. Balloon catheter 500 comprises a elongate, flexible tube 502, having a proximal end 504, a distal end 506 and a lumen 508 therebetween. The distal portion of the tube 502 has a balloon formed thereon with a passage extending therefrom proximally through the sidewall of the flexible tube 502. An attachable/detachable magnet unit 510 is disposed on the distal end of the tube 502.

As shown in FIG. 18, the magnet unit 510 comprises a distal magnet element 512, having a passage therethrough, and an annular proximal magnet element 514. The magnet elements 512 and 514 can be made of a permeable magnetic material, such as hiperco, or a permanent magnetic material such as neodymium-iron-boron. The magnet elements can be separated by a flexible element, such as coil 516. The coil 516 can be made of a magnetically responsive material, such as hiperco if desired. The coil 516 can alternative be made of, or coated with, a radiopaque material such as gold. The magnet unit 510 is coated in a polymeric material, which can be lubricated on the outside to facilitate passage through the body.

The unit 510 can be attached to the distal end of the tube 502 at the time of manufacture, or it can be provided separately for retrofitting to existing balloon catheters, to make them magnetically navigable. The unit 510 can be permanently affixed to the distal end of the catheter with adhesive, ultrasonic welding, or permanent mechanical fasteners, or the unit 510 can be removable attached to the distal end of the balloon catheter, with a releasable adhesive, or a releasable mechanical fastener.

The lumen 508 through the tube 502 and the passage through the magnet unit 502 accommodate a guidewire to facilitate navigation through constricted portions of the vasculature.

What is claimed is:

1. A magnetically guidable angioplasty catheter comprising
   an elongate flexible member having a proximal end and a distal end, and
   an expandable element adjacent the distal end for selectively expanding the lumen of a blood vessel in which it is disposed, and
   a magnetically responsive element on the distal tip of the elongate flexible member, sized and spaced distally, relative to the expandable element to be able to orient the distal end of the elongate flexible member and the expandable element in a desired direction in an operating region inside a subject's body, upon the application of a magnetic field from an external source magnet.

2. The magnetically guidable angioplasty catheter according to claim 1 wherein the magnetically responsive element is sized and spaced relative to the expandable element to be able to orient the distal end of the expandable element in a desired direction in an operating region inside a subject's body, upon the application of a magnetic field of about 0.2 T or less.

3. The magnetically guidable angioplasty catheter according to claim 1 further comprising a core wire extending through the distal end portion of the elongate flexible member and the expandable element, the distal end portion of the core wire tapering in the distal direction at least in the distal end portion of the catheter.

4. A balloon catheter comprising an elongate tube having a proximal end and a distal end, and a lumen therebetween, and a balloon at the distal end of the elongate tube, in fluid communication with the lumen, and a magnetically responsive element at the distal tip of the balloon catheter sized, shaped, and spaced distally relative to the balloon to be able to orient the distal end of the balloon catheter in an operating region in a subject upon the application of a magnetic field from an external source magnet.

5. The balloon catheter according to claim 4 further comprising a coil of magnetically responsive material between the balloon and the magnetically responsive element.

6. The balloon catheter according to claim 5 wherein the coil of magnetically responsive material includes a radiopaque material.

7. The balloon catheter according to claim 5 wherein the proximal end of the coil extends into the balloon.

8. The balloon catheter according to claim 7 wherein the coil of magnetically responsive material includes a radiopaque material.

9. The balloon catheter according to claim 4 further comprising a flexible, radiopaque member between the balloon and the magnetically responsive element.

10. The balloon catheter according to claim 9 wherein the flexible, radiopaque member is a coil of radiopaque material.

11. The balloon catheter according to claim 9 wherein the flexible, radiopaque member extends at least partly into the distal end of the balloon.

12. The balloon catheter according to claim 4 further comprising at least one radiopaque marker band for identifying the position of the balloon.

13. The balloon catheter according to claim 12 wherein there is a radiopaque marker band intermediate the proximal and distal ends of the balloon.

14. The balloon catheter according to claim 12 wherein there is a radiopaque marker band at least one of the proximal and distal ends of the balloon.

15. The balloon catheter according to claim 14 wherein there is a radiopaque marker band at both the proximal and distal ends of the balloon.

16. The balloon catheter according to claim 4 further comprising a core wire in at least a portion of the lumen of the elongate tube, the core wire tapering from at least a point proximal to the balloon, to the distal end of the balloon.

17. The balloon catheter according to claim 16 further comprising a proximal tube at the proximal end of the elongate tube, and wherein the core wire extends generally from the proximal tube to the distal end of the balloon.

18. The balloon catheter according to claim 16 further comprising a proximal tube at the proximal end of the elongate tube, and wherein the core wire extends through to the proximal end of the proximal tube.

19. The balloon catheter according to claim 4 wherein the balloon is formed integrally from the wall of the elongate tube.

20. The balloon catheter according to claim 4 wherein the balloon is formed separately from the elongate tube and is secured thereto.

21. The balloon catheter according to claim 4 further comprising an expandable stent on the exterior of the balloon.

22. The balloon catheter according to claim 4 further comprising at least one magnetically responsive element inside the balloon.

23. The balloon catheter according to claim 4 further comprising at least one magnetically responsive element inside the balloon, whose position can be moved relative to the length of the balloon.

24. The balloon catheter according to claim 23 wherein the at least one magnetically responsive element inside the balloon is mounted on a wire in the lumen of the elongate tube so that movement of the wire moves the at least one magnetically responsive element.

25. A catheter for use in opening a vessel occlusion comprising
an elongate flexible tubular member having a proximal and distal end;
a lumen extending between said proximal and said distal end;
a core member that is smaller than the elongate flexible tubular member and having a proximal end connected to the distal end of the elongate flexible tubular member and extending distally beyond the distal end of the elongate flexible tubular member;
an inflatable balloon having a first end secured to the distal end of the elongate flexible tubular member and a second end connected to the core member, the inflatable balloon surrounding the core member and being in fluid communication with the interior passage of the elongate flexible tubular member;
at least one magnetically responsive element attached to a distal tip of said core member and spaced distally relative to the inflatable balloon, to orient the distal end of the core member in a desired direction inside a subject's body upon application of a magnetic field from an external source magnet outside the subject's body.

26. The catheter according to claim 25 above where the at least one magnetically responsive element is positioned on the core member distal of the elongate flexible tubular member.

27. The catheter according to claim 26 wherein the inflatable balloon is made of a high strength polymer balloon material that can withstand up to 25 ATM of pressure.

28. The catheter according to claim 25 wherein an expandable endovascular stent is disposed over the inflatable balloon.

* * * * *